(12) United States Patent
Vasquez

(10) Patent No.: US 10,596,205 B2
(45) Date of Patent: *Mar. 24, 2020

(54) TOPICAL MEDICAMENT FOR SKIN AND MUCOSAL INJURIES

(71) Applicant: REV PHARMA Corp., Miami, FL (US)

(72) Inventor: Efrain Ramon Vasquez, Lujan de Cuyo (AR)

(73) Assignee: REV PHARMA Corp., Miami, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/211,179

(22) Filed: Dec. 5, 2018

(65) Prior Publication Data

US 2019/0105357 A1    Apr. 11, 2019

(51) Int. Cl.

| | |
|---|---|
| *A61K 35/644* | (2015.01) |
| *A61K 9/00* | (2006.01) |
| *A61K 47/06* | (2006.01) |
| *A61K 9/06* | (2006.01) |
| *A61K 31/07* | (2006.01) |
| *A61K 31/355* | (2006.01) |
| *A61K 31/59* | (2006.01) |
| *A61K 36/87* | (2006.01) |
| *A61K 36/537* | (2006.01) |
| *A61K 36/55* | (2006.01) |
| *A61K 36/63* | (2006.01) |
| *A61P 17/00* | (2006.01) |
| *A61K 35/06* | (2006.01) |
| *A61K 47/10* | (2017.01) |

(52) U.S. Cl.
CPC .......... *A61K 35/644* (2013.01); *A61K 9/0014* (2013.01); *A61K 9/06* (2013.01); *A61K 31/07* (2013.01); *A61K 31/355* (2013.01); *A61K 31/59* (2013.01); *A61K 35/06* (2013.01); *A61K 36/537* (2013.01); *A61K 36/55* (2013.01); *A61K 36/63* (2013.01); *A61K 36/87* (2013.01); *A61K 47/06* (2013.01); *A61K 47/10* (2013.01); *A61P 17/00* (2018.01)

(58) Field of Classification Search
None
See application file for complete search history.

(56) References Cited

U.S. PATENT DOCUMENTS

| | | | |
|---|---|---|---|
| 6,440,437 | B1 | 8/2002 | Krzysil et al. |
| 7,357,923 | B1 * | 4/2008 | Vasquez Lipi ....... A61K 9/0014 424/78.06 |
| 8,795,735 | B1 | 8/2014 | Carter |
| 10,016,466 | B2 * | 7/2018 | Vasquez ................. A61K 35/06 |
| 2001/0003753 | A1 | 6/2001 | Farber |
| 2008/0193552 | A1 | 8/2008 | Vasquez Lipi |
| 2009/0162304 | A1 * | 6/2009 | DiLeva .................. A61K 8/678 424/62 |
| 2012/0308670 | A1 * | 12/2012 | Vazquez Lipi ...... A61K 9/0014 424/667 |

FOREIGN PATENT DOCUMENTS

WO    2010/082092    7/2010

OTHER PUBLICATIONS

U.S. Appl. No. 16/011,195, filed Jun. 2018, Ramon Efrain Vasquez.*
International Search Report issued for PCT/US2015/06055 of Record in parent application 15525629.
Kubanov, et al. Modern methods of the treatment of hereditary epidermolysis bullosa. Vestnik Dermatologii 1 Venerologli, 2014, No. 6, pp. 47-56 English traslation;of Record in parent application 15525629.
Written Opinion issued for PCT/US2015/06055 of Record in parent application 15525629.
Extended European Search Report for EP 15860878.6 of Record in parent application 15525629.

* cited by examiner

*Primary Examiner* — Michael Barker
(74) *Attorney, Agent, or Firm* — Neifeld IP Law

(57) ABSTRACT

Dental, vaginal and anal cream composed of exclusively natural active principles containing glycerides and Vitamin A and D, easily retained and preserved when in contact with the inflamed mucosa due to its adhesive mucosal base.

2 Claims, No Drawings

TOPICAL MEDICAMENT FOR SKIN AND MUCOSAL INJURIES

FIELD OF THE INVENTION

A topical ointment for treating skin injuries and mucous disorders.

BACKGROUND OF THE INVENTION

A topical medication for injuries and skin diseases disclosed in U.S. Pat. No. 7,357,923 is a completely natural product to prevent tooth decay covering health care and medical treatment of gum diseases such as gingivitis and periodontitis and for the treatment of oral soft tissue lesions.
Dental Caries Dental caries is referred as an infectious, multifactorial disease characterized by the demineralization, dissolution and degradation of the mineral matrixes of the dental tissues. Dental caries is currently the most common disease affecting the human race and is described as a usual disorder which is today the second most prevalent disease after the ordinary cold. Since ancient times, man has been concerned with tooth decay and recurrent caries to allow the tooth to develop its constant and fundamental role. This disease remains as one of the main public health concerns worldwide.

Dental caries involves interactions at length between susceptible tooth surfaces and cariogenic bacteria due to the availability of a fermentable carbohydrate source, especially sucrose. The simple carbohydrates (example sucrose) are fermented by the bacteria. This causes the pH to decrease and results in demineralization of hard tooth tissues. The acids produced by bacterial fermentation in dental plaque dissolve the tooth mineral matrix. A reversible chalky-white appearance stain on the tooth surface is the first manifestation of the disease which can lead to cavitation if the mineral continues to be exposed to the acid challenge.

The caries formation starts as small demineralized regions on the enamel surface and can progress through root surface dentine to the pulp. The demineralization is caused by acid attack, particularly lactic acid, following fermentation of dietary carbohydrates and oral microorganisms. The lesion formation involves the dissolution of the enamel, the removal of calcium and phosphate ions and transportation to the surrounding environment.
Periodontal Diseases Gingival and periodontal diseases are the second oral health problem worldwide.

Gingivitis caused by bacterial plaque is defined as inflammation of the gingiva characterized by loss of connective tissue attachment. Clinical examples include redness, gum contouring changes, bleeding when stimulated and spongy tissue. This is caused due to ulceration and thinness of epithelial tissue, active dilatation and thickness of capillary vessels and the sign of inflammation agents. Gingivitis is caused by a number of diseases whose main factor is normally attributed to the simple presence of bacteria. However, there are other forms of gingivitis that are not primarily associated with dental plaque. Systemic diseases such as diabetes and leukemia can exacerbate gingivitis associated with dental plaque, endocrine factors (such as onset of puberty and during pregnancy), the action of pharmacology such as Nifedipine, Cyclosporine and Phenytoin and malnutrition (Vitamin C deficiency).

Gingiva diseases: Dental plaque-induced Gingivitis (without other local contributing factors), Dental plaque-induced Gingivitis with local contributing factors, necrotizing ulcerative Gingivitis, puberty-associated Gingivitis, menstrual cycle-associated Gingivitis, Pregnancy Gingivitis, Pyogenic Granuloma of Pregnancy, Diabetes Mellitus-associated Gingivitis, Leukemia-associated Gingivitis, drug-induced Gingival Hyperplasia, oral contraception-associated Gingivitis, ascorbic acid deficiency-associated Gingivitis.

Periodontal diseases induced by bacterial dental plaque are the most common, even though there are other periodontal diseases.

Non-plaque-induced gingival lesions: *Neisseria* Gonorrhea-associated lesions, *Treponema Pallidum*-associated lesions, Streptococcal-associated lesions, *Mycobacterium tuberculosis*-associated lesions, Bacillary Angiomatosis, Primary Herpetic Gingivostomatitis, Recurrent oral Herpes, Varicella-Zoster infections, Generalized gingival Candidiasis, Lineal gingival Erythema, Histoplasmosis, Hereditary gingival Fibromatosis, Oral Lichen Planus, Bullous Pemphigoid, Pemphigus Vulgaris, Erythema Multiform, Erythematosus Lupus, Lineal IgA Bullous-Dermatosis, Wegener Granulomatosis, Psoriasis, allergic reactions to dental materials (Mercury, Nickel, Acrylic), Toothpaste, Mouthwash, chewing gum additives, food and food additives, gingival traumatic lesions, chemical lesions, physical lesions, thermal lesions.

Periodontitis induced by bacterial plaque stands out clearly in the gingival inflammation, bleeding on probing, fiber insertion loss, bone loss, supra- and/or sub-gingival plaque calculus, periodontal pocket formation and/or gingival recession. Tooth mobility and furcation lesions can be seen and may get to the point of tooth loss.

Periodontitis as manifestations of systemic diseases: hematologic disorders associated with Acquired Neutropenia and Leukemia.

Periodontitis associated with genetic disorders: Cyclic and Congenital Neutropenia, Down Syndrome, Leukocyte adhesion deficiency Syndromes, Papillon-Lefèvre Syndrome, Chediak-Higashi Syndrome, Langerhans cell Histiocytosis, Glycogen storage disease, Chronic Granulomatous disease, Infantile genetic Agranulocytosis, Cohen Syndrome, Ehler-Danlos Syndrome (types IV and VIII), Hypophosphatasia, Crohn disease (Inflammatory Bowel Disease), Marfan Syndrome.

Unfortunately there is still no effective control for these oral infectious diseases. Most current treatments are concerned with rehabilitation for the damage caused and prevention maneuvers approach to increase host resistance through the use of fluorides and eliminate bacterial plaque with pharmaceutical products including active agents such as chlorhexidine gluconate, triclosan, thymol, cetylpyridinium chloride and other such as using alcohol as vehicle and solvent for active ingredients. Even though the preventive properties of fluoride ion are well studied, there is relevant evidence of toxicity ranging from dental fluorosis and more serious dental problems depending on food intake and age. This must be regarded as a medication rather than a cosmetic product. Therefore, the dental health professional (dentist and pediatric dentist) must decide a route of administration, dosing and general guidelines such as gingival status, tooth brushing frequency and fluoride intake found in other food sources (salt, tea, milk and tap water or mineral water).

In order to prevent and/or cure oral bacterial infections, it would greatly contribute to have an effective natural and non-toxic product which could demonstrate high effective levels at any dental development with no oral mucosa irritation, alterations in taste acuity, permanent tooth staining or adverse side effects, notwithstanding the dosage used.

Mucosal and cutaneous lesions of the vaginal and anorectal region

The present invention also provides a completely natural product for topical application for the vaginal and anal mucosa. In particular, this refers to a product that can be formulated as a topical medication for the treatment of a wide variety of skin disorders and lesions as well as mucosa of the above mentioned areas.

For purposes of this invention, the term "skin" is meant to refer to dermis and epidermis, as well as mucosal membranes.

Epidermolysis bullosa (EB) is an inherited connective tissue disease causing blisters in the skin and mucosal membranes after minor trauma, with an incidence of 1/50,000. It is a result of a defect in anchoring between the epidermis and dermis, resulting in friction and skin fragility. Its severity ranges from mild to lethal.

Epidermolysis bullosa simplex is a form of EB that causes blisters at the site of rubbing. It typically affects the hands and feet, and is typically inherited in an autosomal dominant manner, affecting the keratin genes KRT5 and KRT14.

Junctional epidermolysis bullosa is an inherited disease affecting laminin and collagen. This disease is characterized by blister formation within the lamina lucida of the basement membrane zone and is inherited in an autosomal recessive manner. It also presents with blisters at the site of friction, especially on the hands and feet, and has variants that can occur in children and adults.

Dystrophic epidermolysis bullosa (DEB) is an inherited variant affecting the skin and other organs. "Butterfly children" is the term given to those born with the disease, as their skin is seen to be as delicate and fragile as a butterfly's wings. DEB is caused by genetic defects (or mutations) within the human COL7A1 gene encoding the protein type VII collagen (collagen VII). DEB-causing mutations can be either autosomal dominant or autosomal recessive.

EB produces blisters or vesicles on the skin which contains serohematic fluid. When these blisters burst they produce injuries similar to burns that evolve, producing multiple scars and retractions of the skin which cause functional disabilities such as pseudosyndactyle, among others. Injuries also appear in membranes and mucosal membranes generating complications through the gastrointestinal tract which causes malnutrition, making healing even harder.

A characteristic of EB is the pronounced fragility of the skin and mucosal areas that lead to the formation of blisters and ulcers in response to minor traumas. The more exposed areas of skin are the ones affected by frequent friction or pressure. The peribuccal tissue, skin and mucous of lips or cheeks are specially affected because they are constantly exposed to chewing trauma. The ulcers produced in the peribuccal area during the chewing process generate scars and the tissues retract causing microustomya, until patients cannot open their mouths.

Even though the complete spectrum of clinical signs is wide: blisters, itching, skin erosions, atrophic scars, hyperqueratosis and ulcers are the main skin expressions of this disease.

Simple EB is diagnosed at birth; its main characteristic is the formation of blisters after a traumatic event, frequently in the palms of the hands, elbows, and soles of the feet. Blisters could be flaccid and when they burst they leave a melceric scab. Blisters are of erythematous base due to friction, and exacerbated by perspiration and excessive heat.

Joint EB presents blisters of generalized distribution, hyperplasic granulation tissue in the perioral, perinasal and groin regions or in the locations of the blisters. It affects the mucous of the mouth (intraoral vesicles) larynx, bronchus, esophagus, recto and vagina. Extended denudated areas in places of friction. Combination of chronic infections and loose of iron through the skin can turn into a chronic anemia.

Dystrophic EB presents blisters, either localized or generalized; when they disappear they leave dystrophic scars. Big denudated skin areas could be seen in places like the thorax. Blisters appear spontaneously in any place, being more frequent in friction areas. In addition, they could suffer from pseudosindactilia. Among complications they may suffer Espino cellularaggressive carcinoma. The formation of vesicles all over the body may result in the loss of body fluids, electrolytes, blood and proteins; dehydration, anemia and slow growth.

Known methods of treatment for EB are only partially effective. They focus on treating the pain and bacterial infections associated with injuries of the skin, but no definitive treatment exists today. The known treatments are symptomatic and palliative, focusing on preventing the development of injuries and their complications, e.g., draining blisters, using creams containing antibiotics, antiseptic agents and silicone patches. These prior art treatments do not provide a satisfactory therapeutic effect. For instance, when gauze dressings or silicone bandages are pulled off they may cause some harm to healthy skin around the wounds due to their adherence level, and leave suppuration in the area that must be removed by mechanical means (e.g., cleaning them with gauze), which slows the healing process.

Finding a treatment that can provide proper healing of the injuries produced by EB is a challenge that medical science has not achieved.

The present invention provides a non-toxic topical ointment based on natural ingredients which can provide high therapeutic efficiency for the injuries described above and diminish the many complications of EB.

A topical ointment for treating injuries and skin disorders is disclosed in U.S. Pat. No. 7,357,923 (Vasquez Lipi) for the treatment of a wide variety of skin injuries which is suitable for use on mucous surfaces. This ointment is composed of an oleaginous base, olive oil, sunflower oil, almond oil, castor oil, mineral oil and virgin beeswax as primary ingredients.

SUMMARY OF THE INVENTION

1. An object of the invention is to provide a composition for application to dental, vaginal or anal surfaces, comprising:

comprising:
  about 15% to about 30% petroleum jelly,
  about 5% to about 10% cod liver oil,
  about 15% to about 30% beeswax,
  about 5% to about 10% flax seed oil,
  about 5% to about 10% grape seed oil, and
  about 5% to about 10% chia oil,
a pharmaceutically-acceptable excipient for topical application to skin, and a preservative. Optionally, the composition may contain about 5 to 10% olive oil.

Another object of the invention is to provide a method for treating lesions of dental, vaginal or anal surfaces, comprising:
  a) applying to skin or mucosal surfaces of a patient in need of treatment for EB a dressing gauze or bandage without prior cleaning of said skin or mucosal surfaces, wherein distributed on said dressing is an effective amount of a composition containing: from about 15 to about 30 percent by weight of beeswax; an oleaginous base, an added vitamin selected from the group consisting of vitamin A, D and E; and a pharmaceutically acceptable excipient and a preservative;

b) removing said dressing at least twice per day without damaging the patient's skin or mucosal surfaces due to removal of the dressing. The more often that the dressings are changed the faster the wounds heal.

It is important to understand that changing the dressings twice a day is only possible because of the ointment's benefits, i.e., there is no pain, and the gauze does not stick to the tissue. With prior art treatments the dressings are generally changed every two days, or else they give morphine to the patients to bear the pain of more frequent dressing changes.

DETAILED DESCRIPTION OF THE PREFERRED EMBODIMENTS

The invention hereinafter called DENTAL PROTECTOR (DP) is a dental cream that prevents colonizing bacteria, prevents tooth decay and speeds up the healing process of oral diseases affecting soft tissues, either by the incidence of bacteria or caused by a traumatic injury. Dental cream containing no chemical synthesis elements.

Tooth or Bacterial Plaque

Bacterial plaque, easily spotted on the teeth, is white, grayish or yellowish and has a globular appearance. Determinant factors are oral hygiene and host-related elements such as diet, salivary components and salivary flow rates.

There are three phases of formation of dental plaque: formation of a pellicle coating on the dental surface, initial colonization, secondary colonization and plaque maturation.

1—Formation of a pellicle coating: initial phase of plaque development. Every oral area such as mucosal surfaces and dental restoration surfaces, fixed or removable prosthetic dentistry, is covered with a glycoproteins pellicle. This pellicle arises from salivary components, fluid from gingival troughing, bacterial debris and bacterial products and host tissue cells.

On the enamel surface, formed by HAP crystals (hydroxyapatite), the mechanism of acquired pellicle formation is based on the interaction of electrostatic forces (van der Waals forces) and hydrophobic forces. The hydroxyapatite surface (phosphate groups predominant) is a negatively charged surface which interacts with salivary macromolecular elements whereas the trough fluid gives out positive charge.

Functions of dental pellicle:

Protection barrier: protects surfaces and prevents tissue desiccation.

Serves as a substrate where bacteria proliferates and progressively accumulates to form dental plaque.

2—Initial colonization of the dental surface.

Within a few hours, the dental pellicle shows facultative gram-negative microorganisms such as *Actinomyces* viscous y *Streptococcus sanguis*. These adhere to the pellicle by means of molecules called adhesins found on the bacterial surface and adheres through specific interactions to proline rich proteins found on dental plaque. Thus the bacterial cell binds to the tooth surface covered by the pellicle. The plaque mass matures due to the growth of bacterial species attached to it. In this ecological succession of the biofilm, there is a transition from the early aerobic environment characterized by Gram-positive facultative species to a highly oxygen deprived environment in which Gram-negative anaerobic microorganisms predominate.

3—Secondary colonization and plaque maturation.

This phase occurs by the colonization of the additional bacterial species that do not adhere to the clean tooth surface. Germs such as intermediary *Prevotella, Prevotella loescheii, Capnocytophaga, Fusobacterium Nucleatum* and *Porphyromonas gingivalis* adhere to the other bacteria which are already present in the initially colonized plaque mass by a process of co-aggregation.

The main oral diseases caused by bacteria are caries and periodontal diseases. These diseases are considered the most prevalent human diseases affecting 80% of the world population. Given the proven relationship between the periodontal disease and cardiovascular diseases, the periodontal disease must be considered a public health problem worldwide.

DP Advantages

This invention provides a non-toxic toothbrush composed of natural ingredients that do not represent cumulative damage in time and that can provide high-efficiency preventive and therapeutic treatment of bacterial infectious diseases such as caries and periodontal disease. Besides, as DP does not contain toxic active components, this product can be used in every stage of the tooth development and does not produce irritation of the mucosa or alterations in taste acuity.

A topical ointment for the treatment of lesions and skin disorders, U.S. Pat. No. 7,357,923 (Vasquez Lipi), for the treatment of a wide variety of skin lesions suitable for use on mucosal surfaces.

(DP) Properties:

Formation of an oral surface bound complex which originates a protective layer that prevents bacteria attack.

The Hap particles (hydroxyapatite) have negative electric charge on surface and are attracted by similar calcium ions coming from saliva for their neutralization. Bearing in mind that the lipids prevalent contain negative electric charge, electrostatic interactions with calcium are produced with such lipids being absorbed onto HAp.

Through the action of free fatty acids DP achieves to:

Inhibit the production of acids through the microorganisms of the oral biofilm.

Reduce colonies of bacteria on tooth forming a hydrophobic coating.

Inhibit *S mutans*, the major cariogenic bacteria within the microbial community in a dental biofilm.

Reduce the enamel caries and diminish the cariogenic properties of an *S. mutans* in biofilms after exposure to sucrose.

Inhibit *S. mutans* growth and the *S. mutans* metabolic pathways.

Induce biofilms with a lower quantity of bacteria.

Produce an anticariogenic effect interacting with the plasma membrane of the bacterial cell which prevents the adherence and the bacterial metabolism.

Reduces biofilm biomass.

Reduces the demineralization on enamel induced by sucrose.

Reduces inflammation.

Mechanism of Action

DP attachment to the tooth surface: the HAp found in enamel and negatively charged carboxylic groups from other oral surfaces are attracted by calcium concentrations in saliva and the negatively charged fatty acids found in DP are also attracted by salivary calcium. Therefore, DP attaches to the tooth surfaces altering and retarding biofilm formation.

Besides, DP free fatty acids favors electrostatic interactions with oral surfaces preventing proper attachment of the glycoprotein film, the main component during the very initial phase of plaque formation. As a result, when brushing teeth with DP and removing biofilm, one prevents and/or retards plaque formation and the spread of oral infectious diseases. This beneficial action is attributed to a change in substrate (dental biofilm) where bacteria attach due to a "New protective barrier".

The "New protective barrier" has a double beneficial role due to their high contents of fatty acid. First it forms a protective film because the new protective barrier lubricates surfaces and prevents tissue dissection. Second, it prevents bacterial colonization and aggregation when altering the membrane of the bacterial cells.

Lipids found in DP retard the diffusion of lactic acid preventing the enamel demineralization and altering the bacterial plaque. This could be observed in many studies published demonstrating that:

1—"The acidogenicity of the biofilm exposed to 10% sucrose and then to free fatty acids such as oleic and linoleic featured lower pH drops in comparison with other biofilms exposed to only 10% sucrose. The biofilm analysis reported a decline in biomass. A significantly lower reduction of enamel demineralization induced by sucrose has been observed when biofilms were treated with oleic and linoleic acids". "The monounsaturated and polyunsaturated free fatty acids applied after a sucrose exposition (10%/u) reduce the enamel caries and diminish the cariogenic properties of an S. *Mutans* biofilm. The same effect has not been observed with saturated free fatty acids" In vitro Giacaman, Mufloz-Sandoval et al 2012.

2—"Animals eating diets rich in linoleic and lauric acid allowed for a biofilm with a lower quantity of bacteria" Williams, Schemehorn et al 1982. It was described that fatty acids owe their anti-cariogenic effect to the interaction with the membrane in bacterial cell, which prevents adherence and bacterial metabolism.

3—"Fatty acids such as oleic and linoleic acids, being listed as lipophilic, would act as antibacterial when affecting the integrity of cell membrane increasing the proton permeability." Osawa, Miyasaki et al 2001, Jeon, Zosalen et al 2011.

4—"Fatty acids would interact with the cell membrane when inhibiting transport across such membrane forming micelles that prevent adherence and bacterial metabolism". Williams, Schemehorn et al 1982, Hayes 1984.

5—"Polyunsaturated and monounsaturated fatty acids reduce inflammation and/or act as antioxidants" Spahis, Vanesse et al 2008, Galli and Calder 2009. Huang, George et al 2010.

6—"Lauric acid is highly bacteriostatic on Gram-positive microorganisms." Kabara, Swieczkowski et al 1972 (in vitro study).

7—"Fatty acids such as oleic and linoleic acids, being listed as lipophilic, would act as antibacterial when affecting the integrity of cell membrane increasing the proton permeability." Osawa, Miyasaki et al 2001, Jeon, Zosalen et al 2011.

8—"Polyunsaturated fatty acids have more than a double bond as they compete for H during the bacterial metabolism whereas bacteria get saturated by polyunsaturated fatty acids reducing the acid production." Thompson and Spiller 1995.

This chemical composition is considered a natural antibacterial agent since it fits the characteristics that suggest application as an anti-plaque agent acting as an adjusting device of the oral micro flora. (Premoli, and others, 2009), (Ortega, Benitez C., & Cabezas F., 2010), (Darby, 2011), (Alzaga, 2011), (Bhateja, Arora, & Mahna, 2013) and (Pereira A., 2014).

EXAMPLE

In order to prevent caries and periodontal disease, apply this dental cream to the toothbrush brushing teeth and gums with conventional hygiene techniques. Then, rinse the mouth thoroughly. For the treatment of gingivitis, periodontitis and gingival retraction, the DP application is direct. First proceed with oral care, apply dental cream and allow to it to react.

In greater lesions extend dental cream with gauze and apply on soft areas.

Treatment of Vaginal Lesions

Topical medication of lubricant, emollient, protective and re-epithelizing action of the cervical vaginal mucosa. This cream acts by forming a film which protects, lubricates and paves the way for the regeneration of tissues providing immediate symptom relief (pain, itching).

This topical medication is composed of yellow beeswax (also known as "Virgin Wax") preferably within a base of pharmaceutical acceptable oilseeds for topical application for the skin or the mucosa. Alternatively, the oilseed base is a mixture of vegetable and animal oils that combined in specific proportions, give rise to a topical medicine which helps speed healing. These natural active principles, fatty acid glycerides, vitamin A and D, do not contain corticosteroids, antibiotics, hormones or synthesis products.

The topical medication is easily retained and preserved when in contact with the inflamed mucosa due to its adhesive mucosal base. Besides, its application does not require complexed and/or painful techniques.

Uses

Post-surgery, labiaplasty, vaginoplasty, etc.
Vulvovaginitis
Benign cervicovaginitis, endocervicitis, cervicopathy
Bleeding following cervical biopsy
Lesions following cryotherapy
Radiotherapy lesions
Atrophic vaginitis in menopause women
Prevents vaginal dryness and pain during intercourse when the vaginal mucosa is altered
Vaginal lubricant in perimenopause women Vaginitis "Gram-positive *Lactobacillus*" (also known as Döderlein *bacillus*) is defined as the vaginal microflora of healthy women which includes other aerobic and anaerobic microorganisms that inhabit the lower genital tract.

There are variations of the vaginal microflora based on age and vaginal tropism, pH and the action of estrogens on the vaginal epithelium. In fact, estrogens promote the acid pH (3, 5 and 4) that would prevent the appearance of pathogens.

Vaginitis is a usual and greatly extended disease, but not easily understood in all its aspects. There are predisposing factors (antibiotic therapy, stress, corticoids, oral contraceptive methods, IUD, diabetes, etc.) that help aggravate this infectious syndrome.

In all these cases, this topical medication has demonstrated to be useful in the treatment of vaginitis of different etiology and has improved any type of inflammatory processes. Therefore, it helps diminish vaginal burning, itching and dyspareunia.

This topical medication shows excellent tolerance in genital processes tending to restore the bacteriologic balance in patients with non-specific vaginal discharge. It does not produce any type of local or systemic side effects.

Bleeding Following Lower Genital Tract Biopsies

The practice of biopsying lesions affecting the lower genital tract (cervix, vagina and vulva) is a practice of wide and frequent use at medical consulting rooms.

This procedure usually causes copious and persistent bleeding showing increased risk in lesions with great inflammatory component or in pregnant women, most of all in a usually infected environment. Wound cicatrization gets normally complicated in an inadequate vaginal atmosphere. Moreover, the usual bacterial virulence is significantly increased due to the alkalinity caused by the frequent loss of blood. In all these processes this topical medication acts first as hemostatic, stopping the bleeding in a few minutes and as re-epithelizing assuring the cicatrization and favoring the restoration of the natural acid media.

Treatment of Anorectal Lesions

The application of this topical use medication in mucocutaneous anorectal lesions include:
Hemorrhoids
Anal fissures
Anal and perianal ulcers
Post-surgery
Papillae cryptitis
Anal dermatitis Overview
Patients affected with anorectal disorders are generally embarrassed about their condition and reluctant to visit a physician.
It is believed that 35% of the adults have suffered or suffer from some form of anorectal disorder. Most common diseases include anitis, hemorrhoids and anal fissures.
Common causes include constipation and its treatment, diarrhea, poor diet, antibiotic therapy, different type of local anal lesions, parasitosis, family genetic predisposition, sedentary habits, obesity, portal hypertension, poor hygiene methods, etc.
Most common symptoms include pain, pruritus, itching, tenesmus, bleeding.
Most common treatments include anti-inflammatories, anxiolytics, vitamins, antibiotics, a variety of surgical procedures. These treatments have their own disadvantages and side effects and are expensive and long-term treatments that dishearten patients.

Most products commercialized in the market are drug interactions and include corticosteroids and anesthetics, both chemical groups showing their characteristic side effects.

Moreover, all of them contain exclusive symptomatology effects and do not comply with the therapeutically conditions required by the anorectal pathologies such as anti-infectious, anti-inflammatory and re-epithelizing.

The chemical groups mostly used are:
1. Corticosteroids: most commonly used. Corticosteroids are palliative care since the cause of illness does not disappear but they do suppress the inflammatory reactions. Therefore: corticoids can mask the disease process and only improve the inflammatory condition and symptoms. Some infectious pathologies can worsen the situation with their use. They are skin absorbed and get into the blood stream with the subsequent risks and adverse side effects. Corticoids can retard the normal restoration process of the skin and mucosa in general, can cause dermatitis and are not recommended during pregnancy, post-partum and breastfeeding.
2. Local anesthetics are drugs that when locally applied inhibit the transmission of the sensitive impulse. Through absorption anesthetics can get into the blood stream causing CNS stimulation producing restlessness, tremor, drowsiness or dizziness. Another disadvantage is that when administering a local anesthetic to the area, the skin is deprived of the sensitive control which spurs patient to avoid effort, pressure, traumatisms, etc. aggravating the disease.
3. Antibiotics are one of the main reasons of anal pruritus (itchiness), can cause diarrhea and are often unnecessary.

This topical medication is 100% natural, composed of natural origin glycerides, Vitamin A and Vitamin D, has no side effects and quickly relieves the most common symptoms such as inflammation, pruritus, pain, burning and bleeding.

It acts as a whole because in addition to its wide re-epithelizing capacity, this topical ointment has evident anti-inflammatory and anti-infectious properties.

It is a totally safe-for-use product since it has no corticoids, antibiotics, hormones or anesthetics.

Re-Epithelizing Effect

The anti-infectious, anti-inflammatory and pH recovery effects are fundamental factors for the protection of the mucosa which favor and speed up the re-epithelization process.

The presence of Vitamin A and Vitamin D, known for their protective action and revitalizing effect, as well as the glycerides (known for their antibacterial and antimycotic properties) define this topical medication as an integral action formulation stimulating granulation tissue formation and restoration and anti-inflammatory and anti-infectious product.

CONCLUSIONS

Balanced combination of natural glycerides and Vitamin A and D of local action.
Safe effective formula different from what has been used today with no chemical synthesis elements (corticoids, lidocaine, antibiotics, etc.).
This topical prescription creates the optimum conditions for the recovery of the anal and perianal area.
It rapidly improves the infectious and inflammatory symptoms of the anal pathological processes and strongly stimulates the re-epithelization and restoration of lesions of tissue or post-surgical injuries.
Sole integral therapy of the cutaneous-mucosa pathology (anorectal, gynecological, dermic and pediatric)

| PROPERTIES | APPLICATION |
| --- | --- |
| Cicatrization | Severe and chronic anal fissures |
|  | Anal and perianal ulcers |
|  | Anal post-surgery |
| Antipruriginous Hemostatic Anti-inflammatory | Hemorrhoid processes |
| Anti-inflammatory | Proctitis or anitis |
| Anti-infectious | Papillitis |
| Analgesic | Cryptitis |
|  | Anal dermatitis |
|  | Pain caused due to anal fissure |

Fundamental Effects of this Topical Medication
Anti-Infectious Effect:
1. Emollient Action The impermeability activity of this topical medication restricts the formation of secretions, a feasible atmosphere which facilitates the microbiotic development leaving the mucosa clean and pink.

2. Astringent Action:

The precipitation of bacterial proteins destroys these germs and contributes to a faster elimination of the surface cells of the assaulted mucosa no longer recoverable that only served as culture medium.

Therefore, this product paves the way for the restoration of the deepest cell layers and for the regeneration of the most superficial cells that enjoy greater vitality.

3. Acidifying Action:

The acidic pH is hostile to the microorganisms but acts as a stimulant for the recovery of the mucosa (1 g).

Anti-Inflammatory Effect:

The protective action exerted on the mucosa has an influx on the blood capillaries decongesting them. It diminishes their exudation and edema, restricts the infection, improves irrigation and tissue oxygenation and the typical symptoms such as burning and pain among others disappear.

The present method of treatment can make use of the ointment disclosed in U.S. Pat. No. 7,357,923, which is incorporated by reference. However, an improved ointment formulation is disclosed herein for topical application to the skin of patients with EB who present blisters, ulcers, itching, skin erosions, atrophic or dystrophic scars, and friction areas where pseudosindactilia are found.

The expression "mucosal surfaces" as used herein includes the mucosal surfaces of buccal area and anal area as well asesophagus, nasal mucosal surfaces. The medicament comprises yellow beeswax (also known as virgin wax) preferably in an oleaginous base pharmaceutically acceptable for topical application to the skin and/or mucosal surfaces of the human body.

The topical medicament disclosed in U.S. Pat. No. 7,357,923 is a mixture of vegetable, animal and mineral oils which, combined in certain proportions, have been found to provide a topical medicament that leads to rapid healing of the blisters, vesicles, ulcers, of itching and pain.

The methods of the present invention are effective for treating dystrophic scars and retractions in the skin which lead to pseudosindactilia and microstomous. The disclosed methods reduce exudate formation and edema, help to clear skin wounds of necrotic tissue and purulent secretions, and encourage the appearance of granulation tissue and re-epithelization. These effects diminish the possibility of developing anemia by loss of secretions with hematic serum of the skin injuries in EB. The present medicament and method of application also possess anti-inflammatory, analgesic, antibacterial hemostatic and emollient properties.

Advantageously, the present method of treatment prevents bandages from adhering to wounds and so the treatment is painless, diminishing the use of analgesics to control pain, orally taken as well as intravenous like morphine. Frequent dressing changes serves to clean the wound of necrotic tissue and dirt, while the antibacterial effects of the ointment helps the skin to heal quickly, enhancing the natural immune defenses of the organ.

The present topical medicament also strengthens healthy skin due to its protective and emollient action, and therefore diminishes skin and mucous fragility which is found in EB. Due to this effect the frequency of blisters, vesicles and ulcers is also diminished. Protective action occurs in both hurt and healthy skin, and prevents harm from chemical, mechanical or physical (wind, friction, cold) irritative effects while diminishing odor and itching and while producing an anti-inflammatory effect.

The topical medicament of this invention forms an impermeable mask over the skin, prevents epidermal drying on conaceus stratus reducing water evaporation from skin surface, turning skin into a moisturized and elastic one.

In the intraoral region the topical ointment of this invention reduces the formation of blisters and vesicles mainly in the tongue and palate, the same as in the peribuccal region, being able to prevent atrophic healings so frequent in EB.

The topical ointments of the invention are able to treat locally the pain due to various and extended wounds of the skin and mucous areas so typical of EB starting from when these patients are born.

When treating am EB patient with a topical ointment of the invention, the ointment should be extended liberally on a gauze to be applied to the skin of the affected area. The dressing should never be unwoven cotton, it should be a gauze or net having small squares that let the skin breath. On top of the gauze a soft occlusive bandage should be placed. When the gauze is applied on the wound the gauze should cover a bigger area around the wound, preferably at least three centimeters extra all around. This bandaging process should be repeated at least twice a day with fresh gauze in the beginning and thereafter less often because of the good results with the treatment. Total duration of the treatment depends on the speed of the individual healing process.

Properties of the Present Invention:
1. Decreases wound pain and provides relief to the patient, facilitating healing, and thus achieving increased patient autonomy.
2. It increases the efficiency of healing, promoting the movement of epithelial tissue in the lesion.
3. Provides a physiological moist environment.
4. Prevents drying of the wound.
5. Reduces infection rates in occlusion protects the wound, providing a bacterial barrier.
6. Stimulates the formation of antimicrobial peptides.
7. Promotes cell migration and promotes angiogenesis.
8. Stimulates the synthesis of collagen and intercellular communication favors.

For minor wounds and healthy skin of EB patients the present topical ointment may be applied directly on the skin According to the present invention, for intraoral treatment of EB wounds like intrabuccal blisters and ulcers, the topical ointment is applied preferably on a gauze in the affected mucous and directly on minor wounds. Topical ointment should be extended on both sides of the gauze and can be placed on the tongue. When the tongue gets in touch with palate a double effect will be reached, it will be treating wounds in the tongue as well as in palate.

For the treatment of gynecological and proctologic conditions, the topical ointment of the present invention is applied using a variety of disposable virginally proctologic appliers easily fund in the market.

Due to the fact that the present ointment is applied in topical form, it is not usual to establish maximum and minimum doses. The amount of ointment to be applied should be related to the extension of the wound. For maximum benefit the wound should be completely covered by the topic ointment.

Very few of the present medicament's ingredients are absorbed by the skin or the mucous surface. Therefore, there are no secondary effects associated with the usage of the present topical medicament. Besides, the ingredients of the topical medicament are natural substances so they are well tolerated locally and systemically.

In one embodiment of the invention, the medicament comprises an oleaginous base of olive oil, sunflower oil, almond oil, cod liver oil, castor oil and virgin wax.

The preferred ointment of the invention comprises, as its primary ingredients, an oleaginous base of petroleum jelly (e.g., Vaseline), cod liver oil and virgin bee's wax, plus flax seed oil, grape seed oil and chia oil.

All embodiments of the invention can be combined with excipients commonly used in the preparation of topically-applied medicaments or cosmetic agents for application to the skin and/or mucosal surfaces of the human body, so as to provide, for example, a cream, gel, lotion or ointment. Preferably, the excipients provide emollient properties.

Preferred compositions according to the present invention contain from about 10 to about 50 percent by weight of virgin wax (yellow beeswax), based on the total weight of the formulation. Preferred compositions also contain Vitamins A, D and E, which can be provided from natural oleaginous sources or as synthetic additives.

In one embodiment, the invention provides a topical product for application to the skin comprising about 5% olive oil, about 21% sunflower oil, about 21% almond oil, about 10%/o cod liver oil, about 3% castor oil and about 23% beeswax, the balance of said product comprising a pharmaceutically-acceptable excipient for topical application to the skin.

In a preferred embodiment, the present invention provides a topical product for application to the skin comprising about 15% to about 30% petroleum jelly, about 5% to about 10% cod liver oil, about 15% to about 30% beeswax, plus 5% to about 10% flax seed oil, plus 5% to about 10% grape seed oil and 5% to about 100/o chia oil, the balance of said product comprising a pharmaceutically-acceptable excipient for topical application to the skin.

The oleaginous base of the ointment may be a mixture of vegetable and animal oils. Olive oil, almond oil, and castor oil are anhydrous vegetable oils made up of liquid or acid, fatty or saturated triglycerides. Olive oil is obtained from the ripe fruit of Oleaeuropaea and its crop varieties. Sunflower oil is obtained from the seed/fruit of *Helianthus annus*, and is known to contain about 75 mg Vitamin E (mixed tocopherols) per 100 g. Almond oil is obtained from the seeds of Prunusamygdalus.

Cod liver oil is the oil obtained from the fresh livers of Gadusmorrhua and other species of Gadidae. The oil is extracted from the liver using steam, which breaks down the cellular membranes. Once obtained it is frozen and filtered to separate the stearin. Cod liver oil contains predominantly glycerides with non-saturated fatty acids that together comprise morrhuic acid. It also contains cholesterol, but the most important constituents are vitamins A and D, i.e., retinol and cholecalciferol or vitamin D3. Cod liver oil is known to contain at least about 850 U.S.P. units (255 .mu.g) of Vitamin A per gram, and at least about 85 U.S.P. units (2.125 µg) of Vitamin D per gram.

Castor oil is the cold-drawn oil of the seeds, stripped of the episperm, of Ricinuscommunis and other members of its family Euphorbisceae. It is a slightly yellow to colorless thick, viscous liquid with mild odor or odorless and subtle taste.

As used herein the term "virgin wax" or "yellow beeswax" refers to the product of fusion and purification of the honeycomb of the Apismellifera (Apidae) bee after the honey has been separated. Preferably, the topical medicament contains between about 10 and about 50 percent by weight of yellow beeswax, more preferably between about 18 and about 27 percent, and even more preferably between about 23 and about 25 percent. Concentrations greater than about 50 percent by weight generally are not preferred because of the solid consistency of beeswax resulting in an undesirably high viscosity or hardness of the final product. Percentages are expressed throughout this application as percent by weight, based upon the total weight of the product, unless otherwise noted.

Flax seed oil, also known as linseed oil, is a colorless to yellowish oil obtained from the dried, ripened seeds of the flax plant (Linumusitatissimum, Linaceae). The oil is obtained by pressing, sometimes followed by solvent extraction. Flax-based oils are sought after as food because of their high levels of α-Linolenic acid (a particular form of omega-3 fatty acid).

Grape seed oil is pressed from the seeds of grapes, and is thus an abundant by-product of winemaking.Grape seed oil contains linoleic acid.

Some of the fatty acids that compose the grape seed oil enhance the beauty are palmitoleic, stearic linolenic, alpha, docosanoic, and icosanoicicosenoic. These fatty acids have many uses for the skin, helping to protect it from the sun, aid in the healing of wounds, reduce varicose veins. Some scientific studies have shown that its antioxidant properties are even greater than those of vitamin C and E, not to mention astringent and antiseptic properties which are good for skin repair. In addition, this oil helps in tissue regeneration. Its capacity to block moisture and repair tissue makes the grape seed oil is very useful and effective.

Chia oil is derived from seeds of *Salvia hispanica*, commonly known as chia, a species of flowering plant in the mint family, Lamiaceae, native to central and southern Mexico and Guatemala. Chia seeds contain a high content of Omega-3 oil (morethan salmon), this oil helps to increase the production of collagen, which acts as an anti-inflammatory agent Omega-3 reduces the appearance of wrinkles and combat acne and other skin imperfections also gives a smooth, youthful look to it.

The most important action of this oil is that it regulates hormones, this is very important because whenever we are victims of our stress hormones are thrown off and your skin may be the first to be affected.

Potassium: This nutrient, like other components of chia seeds, regulates hormone levels, prevents inflammation and swelling of skin and improves our facial muscle activity from it.

Advantageously, the topical medicament of the invention contains Vitamins A, D and E. Synthetic versions of these vitamins can be added during formulation, or, preferably, the vitamins can be added via the inclusion of their natural sources, for example, cod liver oil and sunflower oil. The amounts of these vitamins can be varied, as can their sources. Preferred formulations of the medicaments can contain, per 100 g of the final formulation, between about 1275 and about 3825 µg Vitamin A, preferably about 2550 µg; between about 10.625 and about 31.875 µg Vitamin D, preferably about 21.25; and between about 975 and about 3000 mg Vitamin E, preferably about 2025 mg.

Vitamin A and E: Vitamin E is known for its powerful antioxidant property that produces an anti-aging effect, which prevents wrinkles and fights skin inflammations. It is also used to treat acne scars or decrease the same as it accelerates cell regeneration. Vitamin A also acts as anti-inflammatory, anti-acne producing bacteria. This vitamin regulates the processes of the skin, helping to correct conditions of drying and dehydration, addition, like vitamin E assists in the rapid healing of wounds and protects the skin in general.

The excipients used in the topical medicament of the present invention are comprised primarily of emollients. Emollients are lipids or substances with a similar consistency which, when applied to the skin, protect and soften the skin, making it more supple. Emollients are used primarily as the excipients and bases of ointments and other dermatological preparations. A simple classification of emollients is as follows:

1) Oil-based: Oil-based emollients include fats. These products are anhydrous, do not absorb water and are insoluble in it, and are non-washable. Oil-based emollients include: a) hydrocarbons or mineral fats obtained by the distillation of petroleum (petroleum jelly, e.g., Vaseline); b) vegetable oils and liquid triglycerides: c) animal fats or solid natural triglycerides.

2) Absorbent bases: These bases are anhydrous and insoluble in water, and are hydrophilic. They typically form water-like emulsions in oil and, thus, can incorporate substances in aqueous solutions. In addition, they are largely non-washable. Absorbent bases include: a) Lanolin or wool fats that are obtained from sheep's wool and made up of fatty acids and cholesterol esters; and b) cetyl and stearyl alcohols, which are solid alcohols obtained by hydrogenation of their respective acids.

3) Emulsive bases: These bases absorb-water, but are insoluble in it, forming water emulsions in oil that are not very washable and can be easily removed from the skin. They include surface active agents (surfactants) which improve wetting of surfaces. They include: a) soaps or salts of fatty acids that may be acidic or basic depending on whether the lipophilic group is anionic or cationic; b) sulfated alcohols which are semi-synthetic substances; and c) synthetic surface active agents.

4) Water soluble bases: These bases are anhydrous, absorb water, and are completely soluble in water. They are also non-fatty and washable. For example, glycerin is obtained from fats and, due to its hydrophobicity, has the property of extracting water from the surface of the mucosa or denuded skin. It does not damage intact skin.

When applied to the skin, these substances, which are in general chemically inert, have a protective and emollient action. The protective action occurs on healthy and diseased skin and prevents the effects of chemical, mechanical, and physical (cold, wind) irritants while decreasing burning and pruritus and producing an anti-inflammatory effect. Since these substances form a more or less impermeable layer over the skin, they prevent drying of the epidermis over the stratum corneum by decreasing the evaporation of water from the cutaneous surface. Thus, the skin is softer and more supple. In this way, emollients mimic the natural sebaceous layer that covers normal skin. The bases envisioned for use in the present invention, including the water soluble ones, are well absorbed by the skin, but almost not at all by the epidermis or the sebaceous glands of the hair follicles.

In practicing the present invention, preferably the excipient is comprised of stearic acid and liquid petroleum jelly, with butylhydroxytoluene (BHT) as a preservative and, optionally, herbal essence. Other excipients can be used in lieu of petroleum jelly, such as olive oil, cod liver oil and other natural oils, depending upon the ultimate consistency that is desired which, in turn, depends upon the ultimate use to which the product will be put. Additionally, other preservatives can be substituted for or used in combination with BHT.

Stearic acid is a mixture of solid fatty acids in variable proportions. It is an absorbent, anhydrous, and non-water soluble base which forms water-type emulsions in oil. When combined with the oil bases, stearic acid increases their consistency (viscosity) and makes them hydrophilic. As used herein, the term herbal essence refers to any of the well-known extracts of aromatic plants, such as an aromatic extract of chamomile.

The topical product of the instant invention, which can be in the form of, for example, a cream or an ointment, can be formulated as products specifically adapted for a variety of applications including skin, vaginal, and proctological creams/ointments. Regardless of the specific formulation and the environment in which the product is utilized, the topical product of the invention shows ability to stimulate granulation and re-epithelization and to act as an anti-pruritic surface analgesic and anti-inflammatory agent.

Once prepared, the topical medicament of the invention should be stored in a cool place to maximize its preservation. The final product can be packaged in, for example, 20 g. and 50 g. tubes, or in 50 g., 100 g., 200 g. and 500 g. jars.

The present invention is further described in the following Example, which is provided for illustrative purposes only and is not to be construed as limiting.

Example 1

In order to prepare a 100 g. sample of the topical medicament of the invention, the following ingredients were combined:
PRIMARY INGREDIENTS Olive oil 5.72 g Sunflower oil 21.72 g Almond oil 21.72 g Cod liver oil 10.72 g Castor oil 3.72 g Virgin wax 23.40 g
EXCIPIENT BASE Stearic acid 2.0 g Herbal essence 0.980 g Butylhydroxytoluene 0.020 g Liquid petroleum jelly 10.0 g
Preparation Step 1

The total quantities of the stearic acid and virgin wax are placed in a stainless steel receptacle outfitted with a double casing. The ingredients are heated to 65° C.-70° C. so that the solids melt.
Preparation Step 2

The melted mass is mixed and the total quantity of castor oil, olive oil, cod liver oil, almond oil, and sunflower oil is added to the mixture.
Preparation Step 3

The total quantity of buthylhydroxytoluene is dissolved in the herbal essence and added to the mixture from step 2.
Preparation Step 4

The total quantity of liquid petroleum jelly (or other medically acceptable excipient) is added and the mixture is mixed for 30 minutes while maintaining the heat and, then, cooling slowly with continuous shaking.

Example 2

Cleaning wounds is normally a critical first step for any treatment that does not use a composition of this invention. A cleaning step is used in other treatments to improve the condition of the wound and reduce the risk of infection. However, using the inventive method this cleaning step is avoided. No cleaning is done before application of a bandage containing a composition of the invention, not even cleaning with physiological saline. The dressings described herein act as a wound cleanser. Do not dry the wound or press the dressing. Do not use antiseptics or skin cleansers for cleansing the wound because its cytotoxic power hurts the new tissue. Do not perform drag or pressure irrigation of wounds with any solution, not even saline The inventive method prevents bacterial growth without the cytotoxic effect of the usual antiseptics.

Do not perform debridements because bacterial content, necrotic debris and bleeding from the wound remains in the dressing after it is removed. Action of the inventive composition itself cleans the wound, without any need for aggressive measures that are typical of prior art treatments.

Example 3—Case Report

An approximately 6-month old female patient received treatment according to the present invention for three months. The baby has two heterozygous mutations, c.4007insG in exon 33 and c.8505insC in exon 115 of the COL7A1 gene. Both mutations are frameshift mutations and will lead to the premature termination codons p.Asp1336fsX22 and p.Val2836fsX12, respectively. The patient's mother is a heterozygous carrier of mutation c.8505insC and the patient's father is a heterozygous carrier of mutation c.4007insG. The patient's brother is not a carrier of either of these mutations. Compound heterozygosity for these two frameshift mutations in COL7A1 supports a clinical diagnosis of recessive dystrophic epidermolysis bullosa and the risk for recurrence in subsequent pregnancies is 25%. Identification of both parental mutations means that DNA-based prenatal diagnosis is feasible in the future, if indicated. With regards to the predicted phenotype in this affected individual, a generalised from of RDEB is likely (severe generalized or generalized-other). That said, one of the mutations does occur close to the 3' end of the gene (exon 115 of 118) and therefore if some truncated protein can be synthesized from this mutant allele, a slightly milder phenotype might result—but the diagnosis remains recessive dystrophic epidermolysis bullosa.

The parent's testimonies after 3 months treatment with ointment of the invention:
  Blister occurrence decreased significantly; frequency changed from having new blisters almost every day to just 1 every 25 days.
  Skin color also changed from necrotic maroon to an almost normal health color.
  Most affected areas also decreased.
  The blisters are now free of blood. This allowed our baby to be more happy and relaxed. She showed a dramatic change of mood.
  She is now free of bandages and she can crawl and put her body weight on the hands and knees without risk of blistering
  Since it is a non-toxic product, we feel more comfortable to freely administer it all over her body.
  We also treated her mouth with the product and we also observed a reduction in blister occurrences.
  Cures become more and more simple, thus reducing the healing time.
  Due to the ointment's properties, we can treat our baby just with one single product.
  We foresee a great potential of the product for the treatment of internal mucosal injuries.
  Although the hands healed faster than the feet, the ointment helped to strengthen the skin and make it more elastic.
  The lubricant effect of the product allows us to have more time to share games and have fun with our baby. Thanks to the medication we were able to take off the gloves from her hands and she feels comfortable to play with objects without problem. This is so important because this helped to develop her motor skills.

Indications
  Ointments of the invention are for topical application to the skin of EB patients presenting blisters, sores, itching, skin erosions, dystrophicoratrophic scars, areas of friction and friction pseudosyndactylyin patients with and without skin lesions as well. In the oral mucosa, gastrointestinal mucosa and genital mucosa, in areas with lesions and also in healthy mucosa.

Topical Application
  The ointments of the invention are applied topically, so it is not critical to set a maximum and minimum dose. The amount of the composition to be applied should be adapted to the extent of the injury. For maximum benefit, the lesion must be completely covered by the dressing.
  In treatment of a patient presenting with EB, the ointment is spread in a thin layer on gauze which exceeds lesion by 2 to 3 cm. It is then placed over the affected area. A light occlusive bandage is applied covering the dressing. This regimen is repeated 2 times daily at the start of treatment achieving wound cleansing and adding oxygen to it. Then, the frequency diminishes as a result of a favorable course of treatment. In exchange the lesion swabs should not be affected, one should not clean debris or scrape the tissue. One gauze is replaced by another one without touching the injured skin. The total treatment time depends on how quickly the healing process progresses. In mild lesions and healthy skin of patients with EB, the ointment is applied directly to the skin.
  For intraoral lesions themselves using EB as ampoules and intraoral ulcer, gauze carrying the inventive composition is applied to the affected mucosa and directly, without gauze into minor injuries. The ointment will be extended to both sides of the Cambridge type gauze and subsequently placed on the tongue. As the tongue is in contact with the palate, it achieves the dual purpose of treating injuries both in language and in palate.

The same type of dressing is used irrespective of:
Location of the lesion
Severity of injury
Amount of exudate
Presence of tunneling.
Skin perilesionated
Signs of infection Advantages
  Using active dressings. No use of topical antiseptics, etc.
  Prevents cellular dehydration. Thereby preventing skin dryness forming an impermeable layer thereon, reducing the evaporation of water from the skin surface. So does the skin softness and elasticity.
  Reduces time spent on wound care, thanks to the ease of use of the dressings.
  Promotes insulation.
  Reduces the level of pain. Reduces itching and burning
  Autolytic debridement.
  Faster healing and quality of the healed skin.
  No dystrophic scarring and skin contractures that cause disabling effect spseudosyndactyly or microstomiain EB.
  Reduces the formation of exudates and edema and helps clear skin wounds with necrotic tissue and purulent secretions, thus promoting the development of granulation tissue and re-epithelialization.
  Promotes anti-inflammatory, analgesic, antibacterial, hemostatic and emollient action.
  It does not stick to wounds therefore its use is painless, eliminating the use of pain medication.
  Will not harm healthy skin but has a protective, emollient, thus decreases the fragility of the skin and mucosa observed in EB and in this sense also reduces blisters, vesicles and ulcers. The protective action happens in the diseased skin and healthy skin and prevents damage produced by the chemical irritant effects, mechanical or physical (shear, friction, cold, wind)

In the intraoral region reduces blisters and blisters on the tongue and palate primarily and in the perioral region preventing scarring producing atrophy, so characteristic of the EB.

It is biocompatible. Ointment components are natural substances, mixed vegetable, animal and mineral, with high protein and essential amino acids for healing. Thanks to this natural formula patients have excellent tolerance of the present invention both locally and systemically, with no contraindications for use.

Protect the wound from external aggression

Removes dead tissue absorbing

Leave a minimum amount of waste in the lesion

Secure Grip

Adapts to difficult locations

Easy to apply and remove without pain.

Excellent cost benefit

The invention claimed is:

1. A method for treating lesions of dental, vaginal or anal surfaces, comprising:
    a) applying to internal lesions of mucosal dental, mucosal vaginal or mucosal anal surfaces of a patient in need of treatment for said lesions a dressing gauze or bandage without prior cleaning of said mucosal surfaces, wherein distributed on said dressing is an effective amount of a composition containing: about 15% to about 30% petroleum icily, about 5% to about 10% cod liver oil, about 15% to about 30% beeswax, about 5% to about 10% flax seed oil, about 5% to about 10% grape seed oil, and about 5% to about 10% chia oil, an added vitamin selected from the group consisting of vitamin A, D and E; and a pharmaceutically acceptable excipient and a preservative:
    b) removing said dressing at least twice per day without damaging the patient's mucosal surfaces due to removal of the dressing.

2. The method of claim 1, further comprising about 5% to about 10% olive oil.

\* \* \* \* \*